(12) United States Patent
Seibel et al.

(10) Patent No.: US 7,879,004 B2
(45) Date of Patent: Feb. 1, 2011

(54) CATHETER TIP DISPLACEMENT MECHANISM

(75) Inventors: Eric Seibel, Seattle, WA (US); Per Reinhall, Seattle, WA (US)

(73) Assignee: University of Washington, Seattle, WA (US)

( * ) Notice: Subject to any disclaimer, the term of this patent is extended or adjusted under 35 U.S.C. 154(b) by 834 days.

(21) Appl. No.: 11/610,084

(22) Filed: Dec. 13, 2006

(65) Prior Publication Data

US 2008/0147000 A1 Jun. 19, 2008

(51) Int. Cl.
*A61M 29/00* (2006.01)
(52) U.S. Cl. ............... 604/98.01; 604/528; 604/530; 604/531
(58) Field of Classification Search ............ 604/98.01, 604/530, 531
See application file for complete search history.

(56) References Cited

U.S. PATENT DOCUMENTS

| | | | | |
|---|---|---|---|---|
| 4,686,963 | A | 8/1987 | Cohen et al. | 128/4 |
| 4,688,555 | A | 8/1987 | Wardle | 128/4 |
| 4,695,163 | A | 9/1987 | Schachar | 356/369 |
| 4,758,222 | A | 7/1988 | McCoy | 604/95 |
| 4,762,118 | A | 8/1988 | Lia et al. | 128/4 |
| 4,983,165 | A * | 1/1991 | Loiterman | 604/95.03 |
| 5,381,782 | A | 1/1995 | DeLaRama et al. | 128/4 |
| 5,405,337 | A * | 4/1995 | Maynard | 604/531 |
| 5,507,725 | A | 4/1996 | Savage et al. | 604/95.04 |
| 5,512,035 | A | 4/1996 | Konstorum et al. | 600/146 |
| 5,549,542 | A | 8/1996 | Kovalcheck | 600/146 |
| 6,246,914 | B1 | 6/2001 | de la Rama et al. | 607/122 |
| 6,461,337 | B1 | 10/2002 | Minotti et al. | 604/264 |
| 6,858,005 | B2 | 2/2005 | Ohline et al. | 600/141 |
| 6,932,829 | B2 | 8/2005 | Majercak | 606/198 |
| 2001/0034547 | A1 | 10/2001 | Hall et al. | 623/1.11 |

(Continued)

FOREIGN PATENT DOCUMENTS

DE 44 28 967 C1 12/1995

(Continued)

OTHER PUBLICATIONS

Finci, L; Meier, B; Steffenino, G; Rutishauser, W; "Tandem balloon catheter for coronary angioplasty." Cathet Cardiovasc Diagn, vol. 12, No. 6, pp. 421-425. 1986.

(Continued)

*Primary Examiner*—Nicholas D Lucchesi
*Assistant Examiner*—Pritesh Patel
(74) *Attorney, Agent, or Firm*—Ronald M. Anderson (57) ABSTRACT

A distal end of a flexible catheter can be selectively deflected in a desired direction by actuating one or more actuators that extend outwardly of an exterior surface of the catheter. Each actuator can be a balloon disposed within a non-extendible balloon or sheath. Inflation of one (or both) of the balloon and the non-extendible balloon with a pressurized fluid can deflect the distal tip of the catheter. Another actuator embodiment comprises a strip of a bimorph material that bends outwardly when actuated, e.g., by heat, applying a force against adjacent tissue to deflect the distal tip. Yet another embodiment includes a strip of material that shortens when heated and can be coupled to a balloon that is inflated outwardly to increase a radial moment arm of the force applied thereby, relative to a neutral axis of the catheter, to more readily deflect the distal tip.

34 Claims, 7 Drawing Sheets

U.S. PATENT DOCUMENTS

| | | | |
|---|---|---|---|
| 2002/0100484 A1 | 8/2002 | Hall et al. | 128/898 |
| 2002/0142119 A1 | 10/2002 | Seward et al. | 428/36.9 |
| 2003/0009189 A1 | 1/2003 | Gilson et al. | 606/200 |
| 2003/0236564 A1 | 12/2003 | Majercak | 623/1.11 |
| 2004/0118415 A1 | 6/2004 | Hall et al. | 128/898 |
| 2004/0147827 A1 | 7/2004 | Bowe | 600/374 |
| 2004/0243227 A1 | 12/2004 | Starksen et al. | 623/2.11 |
| 2005/0085693 A1 | 4/2005 | Belson et al. | 600/146 |
| 2005/0171592 A1 | 8/2005 | Majercak | 623/1.11 |
| 2005/0228290 A1 | 10/2005 | Borovsky et al. | 600/466 |
| 2005/0250983 A1 | 11/2005 | Tremaglio et al. | 600/101 |
| 2005/0272975 A1 | 12/2005 | McWeeney et al. | 600/113 |
| 2006/0030753 A1 | 2/2006 | Boutillette et al. | 600/146 |
| 2006/0252993 A1 | 11/2006 | Freed et al. | 600/146 |
| 2007/0270650 A1 | 11/2007 | Eno et al. | 600/145 |

FOREIGN PATENT DOCUMENTS

| | | | |
|---|---|---|---|
| EP | 0 713 672 | | 5/1996 |
| EP | 0 520 388 | | 9/1996 |
| EP | 0 712 032 | | 12/2001 |
| WO | WO 93/20742 | | 10/1993 |
| WO | WO 98/43530 | | 10/1998 |
| WO | WO 01/97902 | | 12/2001 |

OTHER PUBLICATIONS

Yamamoto, H; Sekine, Y; Sato, Y; Higashizawa, T; Miyata, T; Iino, S; Ido, K; Sugano, K; "Total enteroscopy with a nonsurgical steerable double-balloon method." Gatrointest Endosc, vol. 53, No. 2, pp. 216-20. Feb. 2001.

"NASA-Inspired Shape-Sensing Fibers Enable Minimally Invasive Surgery," NASA Tech Briefs, vol. 32, No. 2. pp. 12, 14.

Yoon, W. Jong, Reinhall, Per G., and Seibel, Eric J. "Analysis of Electro Active Polymer Bending: A Component in a Low Cost Ultrathin Scanning Endoscope," pp. 1-26. Published Jul. 2006. University of Washington, Seattle, WA.

* cited by examiner

CATHETER TIP DISPLACEMENT MECHANISM

GOVERNMENT RIGHTS

This invention was made with U.S. Government support under grant No. CA094303 awarded by the National Institutes of Health. The U.S. Government has certain rights in the invention.

BACKGROUND

To more effectively use an ultra-thin catheter, it is generally necessary to steer the catheter through bifurcating ducts and around sharp bends within lumens of a patient's body. For many applications of a catheter that require this capability for steering the catheter, it is necessary to provide an active tip bending mechanism proximate to the distal tip of the catheter, to enable controlled deflection of the distal tip in any desired direction. The conventional approach employed in catheters uses wires for bending a segment of a metal structure at the tip of the catheter, but this approach is considered expensive for small diameter catheters and is much too expensive for single-use catheters that are intended to be discarded after being used one time with a patient. Also, the wires that are employed in this conventional approach for deflecting the distal tip at a desired angle require a relatively rigid case for support, which limits the overall flexibility of the catheter. In addition, space inside an ultra-thin catheter is sufficiently limited to preclude the use of tip bending wires.

Other types of tip bending mechanisms that have been proposed employ shape memory alloy (SMA), shape memory polymer (SMP), or electro-active polymers (EAP) as an internal actuator to bend the distal tip. Typically, as a class of actuators, shape memory materials formed as wire can change shape and/or length when their temperature is changed, which is usually accomplished by heating with an electrical current. Using a different mechanism, electro-active materials change their shape or size when stimulated directly, for example, by application of an appropriate voltage. However, there can be problems when using these types of material internally within an ultra-thin catheter to bend the tip, since the diameter of such a catheter may be too small to provide sufficient bending moment. The torque needed to bend the distal tip generally increases as the length of the moment arm decreases. The moment arm, which is the distance from the neutral axis of the catheter to a point where an actuator applies its force to bend the catheter, becomes very short if the actuator is fully contained within the protective sheathing of the catheter, which is typically less than 3 mm in diameter in ultra-thin catheters. A mechanism that relies upon axial force within the confines of a flexible shaft of a catheter can require more bending force or torque than can be provided by SMA, SMP, or EAP actuators using such a short moment arm. Accordingly, there is a need for an alternative mechanism to selectively bend the distal end of catheters, particularly of ultra-thin catheters using such materials, which is also relatively low cost and simple, and which can provide sufficient force to deflect a distal end of a small diameter catheter to enable steering the catheter around corners within a body lumen or passage. It would also be desirable to employ alternative techniques for deflecting the distal ends of a catheter that are applicable to small diameter catheters.

SUMMARY

Accordingly, as one solution to the problem discussed above, a catheter has been developed having a distal tip that can be selectively deflected in a desired direction. The catheter includes an elongate flexible shaft having a distal end (which also corresponds to the distal tip of the catheter), a proximal end, and an outer surface. An actuator is provided, and at least a portion of the actuator is disposed externally of the outer surface (or sheath) of the catheter. The actuator is selectively actuatable to provide a directed force that causes the distal tip of the catheter to deflect in the desired direction. A source of energy is included for use in selectively actuating the actuator to deflect the distal tip.

In one exemplary embodiment, the actuator comprises a bimorph actuator that has two shape configurations, including a first configuration in which the bimorph actuator is radially compact, and a second configuration in which the bimorph actuator extends radially outwardly from the outer surface of the elongate flexible shaft. The bimorph actuator can comprise a material such as a shape memory alloy (SMA), a shape memory polymer (SMP), a piezo-composite, a strip formed by bonding together two or more dissimilar materials having substantially different coefficients of expansion, or an electro-active polymer (EAP), for example. Another exemplary embodiment includes a balloon that is either embedded in the outer skin of the catheter or is attached to the outer surface of the catheter, and which when inflated, expands axially to produce a force to deflect the distal tip of the catheter.

Optionally, the catheter can include a sheath that covers the free end of the actuator. In the second configuration, the bimorph actuator can then apply the directed force against an interior surface of the sheath, which is configured to transfer the force to any adjacent anatomical structure or tissue within a body of a patient, so as to deflect the distal end of the elongate flexible shaft away from the adjacent anatomical structure in the desired direction. The sheath provides a smooth surface covering the actuator, which facilitates advancement and withdrawal of the catheter through a body lumen, preventing the free end of the actuator from engaging (i.e., "snagging" on) tissue in a body lumen. For example, the sheath can comprise a non-extendible balloon that is disposed around the outer surface of the elongate flexible shaft, encompassing the actuator, but not preventing the actuator from changing shape to extend radially outwardly, when actuated.

In another exemplary embodiment, the actuator comprises a non-extendible balloon. In this embodiment, at least one lumen is included in the catheter and extends proximally through the elongate flexible shaft. The source of energy for selectively actuating the non-extendible balloon can include a source of a pressurized fluid. A valve can be used for controlling the supply of the pressurized fluid to the non-extendible balloon through the lumen, for selectively applying the force to deflect the distal end of the elongate flexible shaft in the desired direction.

In yet another exemplary embodiment, the actuator further comprises a deflector disposed on the outer surface of the elongate flexible shaft and enclosed by a non-extendible balloon. The deflector initiates bending of the distal end of the flexible elongate body in the desired direction by at least initially pushing outwardly against an inner surface of the non-extendible balloon when the pressurized fluid is being supplied to a volume formed between the inner surface of the non-extendible balloon and the outer surface of the elongate flexible shaft. Optionally, the deflector comprises a smaller balloon. A lumen can be included within the elongate flexible shaft for conveying the pressurized fluid from the source to selectively inflate the smaller balloon so that it extends outwardly from the outer surface of the elongate flexible shaft to at least initially push against the inner surface of the non-extendible balloon.

In still another exemplary embodiment, the actuator is attached to a non-extendible balloon (e.g., on its inner surface) and extends in a direction generally parallel to a longitudinal axis of the elongate flexible shaft. The non-extendible balloon is disposed along the external surface of the elongate flexible shaft. The actuator is then selectively energizable while the non-extendible balloon is selectively inflated so that the actuator is then disposed radially further away from a neutral axis of the elongate flexible shaft. When actuated, the actuator shortens in length to apply a force to the elongate flexible shaft through the non-extendible balloon that is inflated; the force applied to a longer moment arm is able to readily deflect the distal end of the elongate flexible shaft in the desired direction.

Another option than can be included on the catheter is a balloon that is configured to expand around the outer surface of the elongate flexible shaft and which is disposed on the external surface of the catheter, proximal of the actuator. A lumen extending through at least a portion of the elongate flexible shaft conveys a pressurized fluid from a pressurized fluid source to inflate the balloon so that a diameter of the balloon increases sufficiently to contact an adjacent anatomical structure within a body of a patient. When the balloon is thus inflated, it exerts a force on the adjacent anatomical structure that stabilizes or anchors the catheter relative to the adjacent anatomical structure while the distal end of the flexible elongate body is being deflected in the desired direction.

This optional balloon to provide an anchor is also usable with a catheter that comprises a mother scope that extends generally from the proximal end of the catheter and which has a distal end that is disposed at an intermediate position along a length of the catheter. A daughter scope then extends distally of the distal end of the mother scope, to the distal end of the catheter, where the actuator is disposed to selectively deflect the distal end of the daughter scope. As a further alternative, the mother scope can include another actuator that is selectively coupled to the source of energy, to selectively deflect the distal end of the mother scope.

When only a single actuator is provided, the elongate shaft can be rotated about its longitudinal axis, to position the actuator in a desired rotational orientation so the when selectively actuated, the actuator deflects the distal tip of the catheter in the desired direction. As an alternative exemplary embodiment, the catheter can be provided with a plurality of actuators that are circumferentially spaced apart around the elongate body. One or more of the actuators can then be selectively actuated to deflect the distal tip of the catheter in the desired direction, and this embodiment does not require that the elongate flexible shaft be rotated to deflect the distal tip in a specific direction.

In some cases, it may be desirable to provide apparatus for deflecting an existing catheter. In this case, an exemplary embodiment includes a collar that is configured to fit over the catheter and which includes one or more actuators that can be selectively actuated to deflect the distal tip of the catheter in a desired direction.

Another aspect of the present technology is directed to a method for selectively deflecting a distal tip of a catheter in a desired direction. The steps of the method are generally consistent with the functions of the components of the catheter discussed above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

DESCRIPTION

Figures and Disclosed Embodiments are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Figure 1:
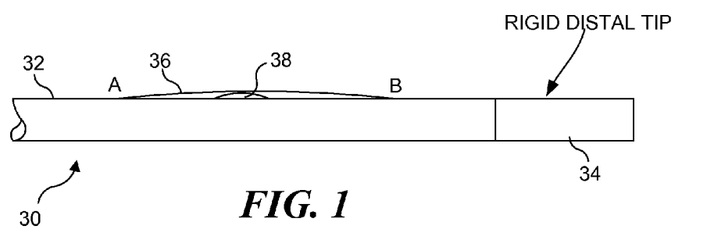
FIG. 1 is a side elevational view of the distal end of a first exemplary embodiment of a catheter that employs the present approach for deflecting the distal tip of the catheter in a desired direction, showing the catheter before any deflection has occurred.
Figures 2, 3, 4, 5:
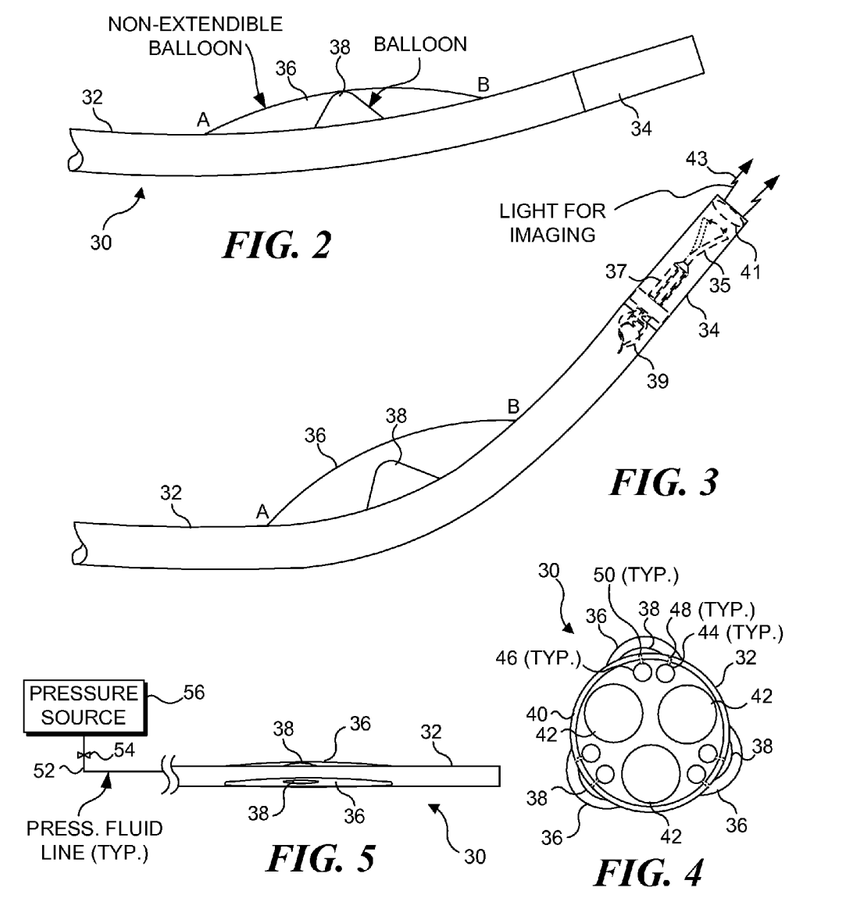
FIG. 2 is a side elevational view of the distal end of the embodiment of FIG. 1, showing a deflector balloon inflated to initiate deflection of the distal tip, as a non-extendible balloon (or sheath) is being pressurized with a pressurized fluid.
FIG. 3 is a side elevational view of the distal end of the embodiment of FIGS. 1 and 2, showing the non-extendible balloon or sheath more fully pressurized to deflect the distal tip of the catheter, and also illustrates an optional imaging device disposed in the distal tip, in phantom view, for use in viewing a pathway ahead of the catheter to aid a user in catheter navigation through body lumens.
FIG. 4 is a cross-sectional view of an exemplary embodiment of a catheter generally like the one shown in FIGS. 1-3, but having a plurality (three) of actuators, each comprising a circumferentially spaced-apart deflector and a non-extendible balloon.
FIG. 5 is a schematic diagram illustrating how one of the non-extendible balloons included in the embodiment of FIG. 4 is coupled to a pressure source through a valve that enables pressurized fluid to be selectively applied to inflate the non-extendible balloon.

FIGS. 1, 2, and 3 illustrate a first exemplary embodiment of a catheter 30 that can be selectively bent to deflect its distal end in a desired direction. Catheter 30 includes an elongate flexible shaft 32 having a rigid distal tip 34. It will be understood that in some embodiments, the distal tip need not be rigid, but can instead be simply the distal portion of elongate flexible shaft 32. It is contemplated the rigid distal tip 34 in some applications can include a scanning optical fiber (not separately shown) for use in imaging a site within a patient's body. However, no limitations in regard to a specific application for catheter 30 are intended.

Catheter 30 includes a non-extendible balloon (or sheath) 36 that is sealingly affixed to the exterior surface of elongate flexible shaft 32 and extends longitudinally between points A and B on the exterior surface. A smaller balloon 38 is also sealingly affixed on the exterior surface of elongate flexible shaft 32, about midway between points A and B and entirely within non-extendible balloon 36. Together, non-extendible balloon 36 and balloon 38 comprise an actuator for selectively deflecting distal tip 34 of catheter 30. In FIG. 1, both non-extendible balloon 36 and balloon 38 are deflated, and elongate flexible shaft 32 remains relatively straight, with its distal tip not deflected. In FIG. 2, balloon 38 has been inflated sufficiently to initiate deflection of distal tip 34 of elongate flexible shaft 32 upwardly, as shown in the Figure. Inflation of balloon 38 applies a force against the interior surface of non-extendible balloon 36, so that the non-extendible balloon applies tension between points A and B, which deflects the distal tip of the catheter. In FIG. 3, pressurized fluid has been supplied to the volume encompassed by non-extendible balloon 36, further deflecting distal tip 34 of elongate flexible shaft 32, in an upwardly direction, by producing more tension between points A and B on the exterior surface of the elongate flexible shaft.

It should be apparent that the selective deflection of elongate flexible shaft 32 can occur in only in a direction that is determined by the disposition of non-extendible balloon 36 and balloon 38 on the exterior surface of the elongate flexible shaft. Accordingly, to deflect the distal tip of elongate flexible shaft 32 in a different desired direction, is necessary to rotate the proximal end of catheter 30 about its longitudinal axis until non-extendible balloon 36 and balloon 38 are disposed on the side toward which the distal tip is to be deflected.

Optional Resonant Scanning Device Used for Imaging

Optionally, an imaging device, such as an exemplary cantilevered optical fiber 35 may be included in distal tip 34 for use in producing an imaging scan downstream of the distal tip. This optional imaging capability can be included in distal tip 34 for any of the different exemplary embodiments of catheters shown in FIGS. 1-3, 6-11, 15, and 23-29 and discussed herein. However, to simplify the Figures for each of these exemplary embodiments, the optional imaging device is only shown in phantom view in FIG. 3. The backscattered light can be collected back through the same optical fiber or using separated collection optical fibers or detected by optical sensors located at the distal tip of the catheter. The image signal is conveyed to the proximal end of the catheter through either optical sensor wires or the one or more collection optical fiber.

By imaging forward of the distal tip, a practitioner can visualize the pathway along which the catheter is to be advanced and more readily selectively deflect the distal tip in an appropriate direction (for example, by selectively actuating a specific actuator to deflect the distal tip). In this way, the practitioner can readily guide the distal tip along the desired pathway within a patient's body.

To produce the image scan in this exemplary embodiment, a piezoelectric tube actuator 37 is activated with signal supplied through electrical leads 39, which extend to the proximal end of the flexible shaft (only a portion of the leads are shown in FIG. 3). At the proximal end of the flexible shaft, the electrical leads are connected to an appropriate signal source (not shown). The piezoelectric tube actuator is activated with the signal supplied through the electrical leads to produce a force that moves cantilevered optical fiber 35 at a resonant (or near resonant) frequency. The resonant behavior of the cantilevered optical fiber produces large deflections of the distal tip of the optical fiber from small piezoelectric tube actuator movements at the base of the cantilevered optical fiber. Light 43 emanating from the distal tip of the cantilevered optical fiber is focused by one or more lens(es) 41 to produce a large FOV scan, such as a spiral scan pattern. Linear scan patterns, and various other space-filling scan patterns other than the spiral scan pattern, such as raster scans and propeller scans, can alternatively be produced by properly modulating the piezoelectric tube actuator drive signals. The light emitted from the distal end of cantilevered optical fiber 35 passes through lens(es) 41 illuminates anatomical features, branches in the body lumen, and more generally, enables visualization of the pathway along which the elongate flexible shaft is being advanced. To produce images that enable this visualization, backscattered light from the pathway can be collected. This light can pass back through the same cantilevered optical fiber, or can be collected by separate collection optical fibers, or detected by optical sensors disposed at the distal tip of the catheter. The image signal produced by the optical detectors is conveyed to the proximal end of the catheter through optical sensor wires (not shown). Alternatively, the backscattered light that was collected by the one or more collection optical fibers can be conveyed to corresponding optical detectors disposed at the proximal end of the catheter. The image signal produced by the optical detectors is used to produce the corresponding image employed for visualizing the pathway being followed by the catheter.

FIGS. 4 and 5 illustrate a variation on the exemplary embodiment shown in FIGS. 1-3, wherein catheter 30 includes a plurality of actuators (three in this exemplary embodiment), each actuator comprising one non-extendible balloon 36 and one balloon 38; the three actuators are disposed at circumferentially spaced-apart positions around the exterior surface of elongate flexible shaft 32, on an outer skin 40 of catheter 30. FIG. 4 illustrates further details of the interior of catheter 30 and how a flow of pressurized fluid is provided to selectively actuate each actuator, for the embodiment having the plurality of actuators, although it should be understood that the configuration of lumens and passages used for selectively supplying pressurized fluid to each actuator in FIG. 4 can be employed, regardless of the number of actuators provided. Specifically, for each actuator, a lumen 44 is provided to convey a pressurized fluid to a radial passage 48, which conveys the pressurized fluid into the volume encompassed by non-extendible balloon 36. Similarly, a lumen 46 is used to convey a pressurized fluid to a radial passage 50 and the pressurized fluid flows through this radial passage and into the volume encompassed by balloon 38. Lumens 42 are included in catheter 30 for conveying other functional components of the catheter (not directly related to deflecting its distal tip), such as optical fibers or electrical leads that are respectively used to carry optical and electrical signals to/from the distal tip.

FIG. 5 illustrates a pressure line 52 that is coupled to the proximal end of one of lumens 44 or 46, and a valve 54 that is selectively opened to supply pressurized fluid from an external pressure source 56 through the pressure line to actuate an actuator by inflating balloon 38 or non-extendible balloon 36. The proximal end of each of lumens 44 and 46 for each actuator is coupled to a similar pressure line and valve (but for simplicity, only one pressure line and valve are shown in the Figure). The external pressure source can be a pressure tank that is filled with a pressurized fluid such as air, or a compressor for compressing air, or can be a pump for pumping a liquid under pressure, such as a saline solution, to increase the volume of the balloon and/or the volume of the non-extendible balloon. In use, the valve on the pressure line coupled to the proximal end of lumen 46 would first be opened to selectively apply the pressurized fluid to balloon 38 to initiate the deflection of the distal tip of the catheter, and once the deflection was thus initiated, the valve on the pressure line coupled to the proximal end of lumen 44 would be opened to supply the pressurized fluid to increase the volume encompassed by the non-extendible balloon to complete the deflection of the distal tip in the desired direction. To achieve the deflection in the desired direction, it may be necessary to actuate a plurality of the actuators. For example, in regard to the disposition of the catheter shown in FIG. 4, the two lower actuators would be actuated to deflect the distal tip of catheter 30 downwardly. Furthermore, the amount of pressurized fluid supplied to one of the two actuators that is actuated can control the direction of the deflection between the two actuators in which the distal tip is deflected.

Figure 6:
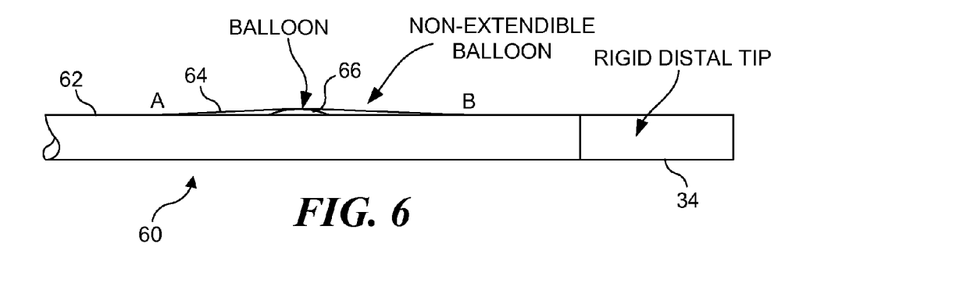
FIG. 6 is a side elevational view of a distal end of an exemplary embodiment of a catheter that employs an actuator having an inner smaller balloon that is inflated to initiate deflection of the distal tip of the catheter, and showing the catheter before its distal tip is deflected.
Figure 7:
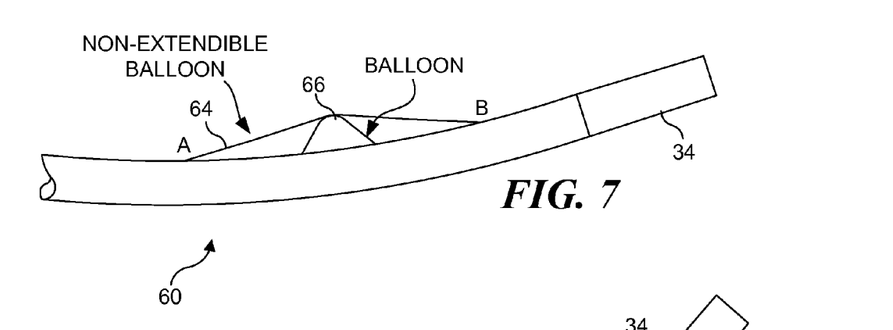
FIG. 7 is a side elevational view of the exemplary embodiment of FIG. 6, with the inner balloon partially inflated, to slightly deflect the distal tip of the catheter.
Figure 8:
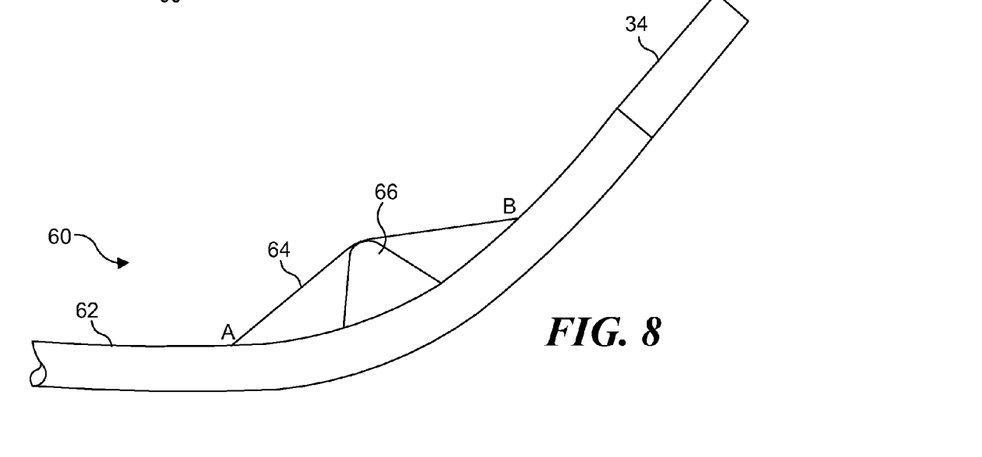
FIG. 8 is a side elevational view of the exemplary embodiment of FIGS. 6 and 7, but showing the inner balloon substantially more inflated, to further deflect the distal tip of the catheter.

A related exemplary embodiment of a catheter 60 is shown in FIGS. 6, 7, and 8. Again, only a single actuator comprising a non-extendible balloon 64 that is sealingly attached to the external surface of an elongate flexible shaft 62 is illustrated in this Figure, but it will be understood that a plurality of such actuators can be provided at circumferentially spaced-apart locations around the elongate flexible shaft. It should also be understood that lumen 44 in FIG. 4 can be coupled to pressure source 56 in FIG. 5 and used to selectively supply pressurized fluid to balloon 66, as discussed above. The primary difference between the exemplary embodiment of FIGS. 6, 7, and 8 and that of FIGS. 1, 2, and 3 is that in the exemplary embodiment of FIGS. 6, 7, and 8, balloon 66 is used not only to initiate deflection of distal tip 34 of catheter 60, as shown in FIG. 7, so that it begins to deflect from the substantially straight configuration shown in FIG. 6, but in catheter 60, balloon 66 is further inflated with the pressurized fluid to apply more force to further deflect the distal tip in the desired direction (and by the desired amount), as shown in FIG. 8. Indeed, a non-extendible sheath can be used instead of non-extendible balloon 64, since it is not necessary to supply pressurized fluid to the volume encompassed by the non-extendible balloon in the embodiment of catheter 60. Instead, the increased volume of balloon 66 and the outwardly directed force that it applies to the inner surface of non-extendible balloon 64 increases the tension between points A and B to cause the desired deflection of the distal tip. In this embodiment, lumen 44 and radially directed passage 48 can be omitted, since it is not necessary to supply pressurized fluid to non-extendible balloon 64 from the pressure source.

Figure 9:
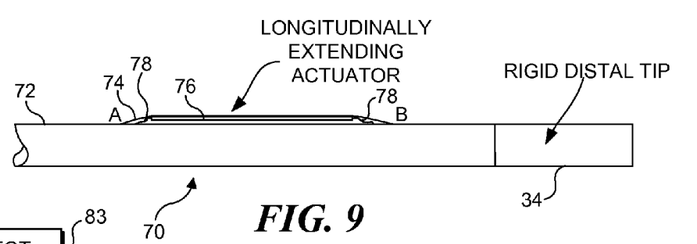
FIG. 9 is a side elevational view of an exemplary embodiment of a catheter that includes a longitudinally extending actuator coupled to an externally mounted balloon, showing the catheter before the actuator is activated to deflect the distal tip of the catheter.
Figure 10:
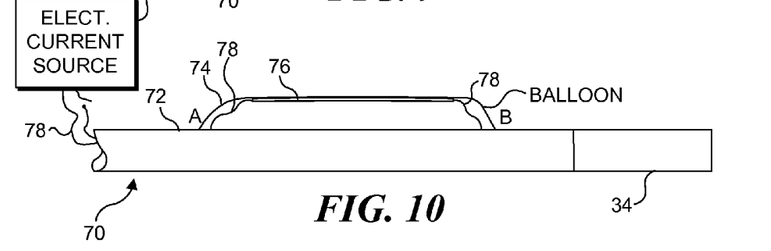
FIG. 10 is a side elevational view of the exemplary embodiment of FIG. 9, after the balloon has been inflated, but before the actuator is activated.
Figure 11:
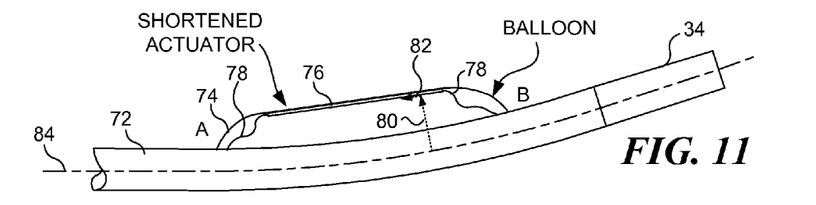
FIG. 11 is a side elevational view of the exemplary embodiment of FIGS. 9 and 10, after the balloon has been inflated and the actuator has been activated to deflect the distal tip of the catheter.
Figure 14:
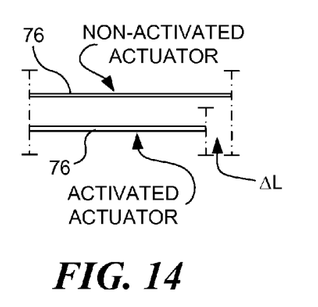
FIG. 14 is a schematic view illustrating the shortening of the longitudinally extending actuator like that used in the exemplary embodiments of FIGS. 9, 10, 11, and 13, which occurs when the actuator is activated.

A catheter 70 illustrates a different exemplary embodiment in FIGS. 9, 10, and 11. For simplicity, only a single actuator 76 is illustrated in each of these Figures. Actuator 76 comprises an elongate strip of a material that shortens in length when actuated by being heated with an electrical current supplied through electrical leads 78. FIG. 14 illustrates how actuator 76 shortens by ΔL when actuated by applying an electrical current that heats the material. Suitable materials for use as an actuator 76 include a shape memory alloy (SMA), a shape memory polymer (SMP), and an electroactive polymer (EAP). Since the force developed as the actuator is heated and shortens in length is not great, for a very small diameter catheter, it may be necessary to increase the length of a moment arm (i.e., the radial distance from a neutral axis of the catheter) to which the force developed by the actuator is applied. The increase in the length of the moment arm 80 is achieved in the exemplary embodiment shown in FIGS. 9, 10, and 11, by coupling actuator 76 to the inner surface of a balloon 74 that that is sealingly attached to and which extends longitudinally along the exterior surface of an elongate flexible shaft 72 of the catheter. When balloon 74 is inflated with a pressurized fluid, the balloon extends outwardly of the exterior surface of the elongate flexible shaft, moving the actuator radially further away from the exterior surface of the catheter and from the neutral axis of catheter 70. The actuator can be adhesively or thermally bonded to the balloon, at least at the opposite ends of the actuator.

FIG. 11 shows the increase in the moment arm 80 relative to a neutral axis 84 (which may initially coincide with the longitudinal axis of the catheter) that results from inflating balloon 74. The increased moment arm increases a torque 82 applied to deflect distal tip 34 of catheter 70, as the shortening of the actuator creates tension in the balloon between points A and B. Electrical leads 78 are attached to each end of actuator 76 to apply the electrical current that heats the actuator so that it contracts in length to develop the force applied as a torque to the elongate flexible shaft.

Figure 12:
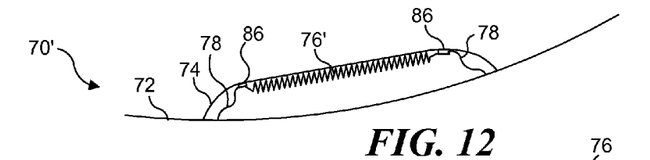
FIG. 12 is partial view of the distal end of a catheter, showing an alternative helical coil longitudinally extending actuator attached to a balloon in an embodiment generally similar to that shown in FIGS. 9, 10, and 11.

FIG. 12 illustrates an alternative embodiment of a catheter 70' (only one side of which is shown) having balloon 74 and an actuator 76' mounted between pads 86, which are mounted on the inside surface of balloon 74. Actuator 76' is formed as a helical coil, for example, of the type of material used for actuator 76. There are differences in the performance characteristics of actuator 76 and 76'. When actuator 76 is actuated, it shortens only about 3-5% in length, whereas actuator 76' shortens by about 30% when actuated, due to the heating caused by an electrical current. However, actuator 76 provides a substantially greater force than actuator 76' when actuated. Accordingly, the use of balloon 74 to increase the moment arm length becomes even more important in catheter 70', than in catheter 70.

Figure 13:
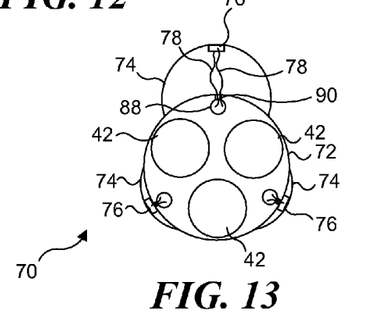
FIG. 13 is a cross-sectional view of an exemplary embodiment of a catheter having a plurality (three) of circumferentially spaced-apart longitudinally extending actuators.

FIG. 13 illustrates an embodiment of catheter 70 having a plurality of actuators (three in this exemplary embodiment), each comprising an actuator 76 coupled to the inner surface of a balloon 74. Lumens 88 are provided within the catheter for conveying electrical leads 78 that enter the catheter through radially extending passages 90. The electrical leads extend through lumens 88 and beyond the proximal end of the catheter, where they are coupled to an electrical current source 83 (two leads used for actuating one actuator with this electrical current source are shown in FIG. 10). As noted above, lumens 42 are included within the catheter, for example, for conveying optical fibers and/or electrical leads used for other purposes, e.g., for scanning an internal site within a patient.

Figure 15:
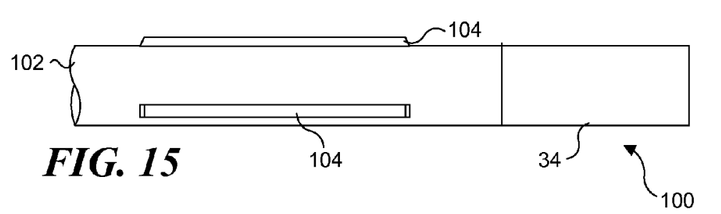
FIG. 15 is a side elevational view of yet another exemplary embodiment of a catheter that includes a plurality of longitudinally extending actuators attached directly to an outer surface of the catheter.

FIG. 15 illustrates an exemplary embodiment of a catheter 100 having an elongate flexible shaft 102 on which elongate actuators 104 are coupled. The elongate actuators extend along an external surface of the elongate flexible shaft and are circumferentially spaced-apart. Unlike the preceding embodiment shown in FIGS. 9, 10, and 11, catheter 100 does not include a balloon that can be inflated to increase the moment arm of the force provided by actuating actuators 104 when heated by an electrical current, which causes the actuators to shorten in length, as explained above. In this case, however, it is assumed that catheter 100 has a sufficiently large diameter so that actuators 104 can provide the required force to the external surface of the elongate flexible shaft to deflect distal tip 34 of the catheter in a desired direction. It should be noticed that the opposite ends of elongate actuators 104 are beveled to minimize the risk that the ends of the actuators may "hang up" on tissue within a lumen of a patient's body when the catheter is being advanced or withdrawn through the lumen.

Figure 16:
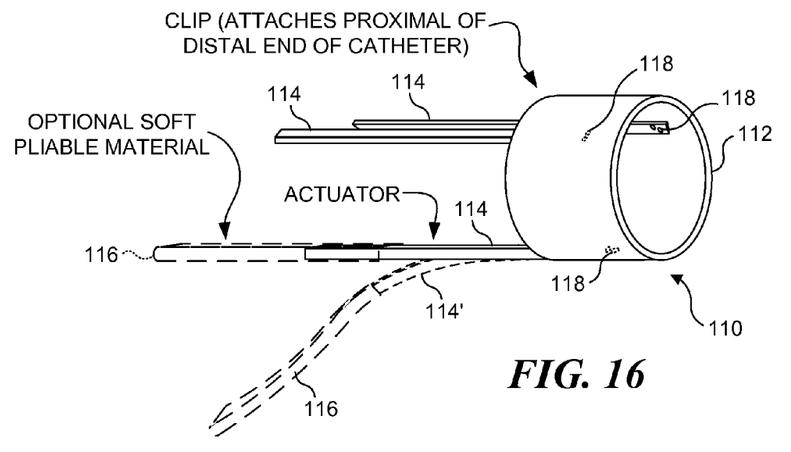
FIG. 16 is an isometric side elevational view of an exemplary collar having a plurality of actuators and configured to be slipped over a catheter and employed to deflect the distal end of the catheter.
Figure 17:
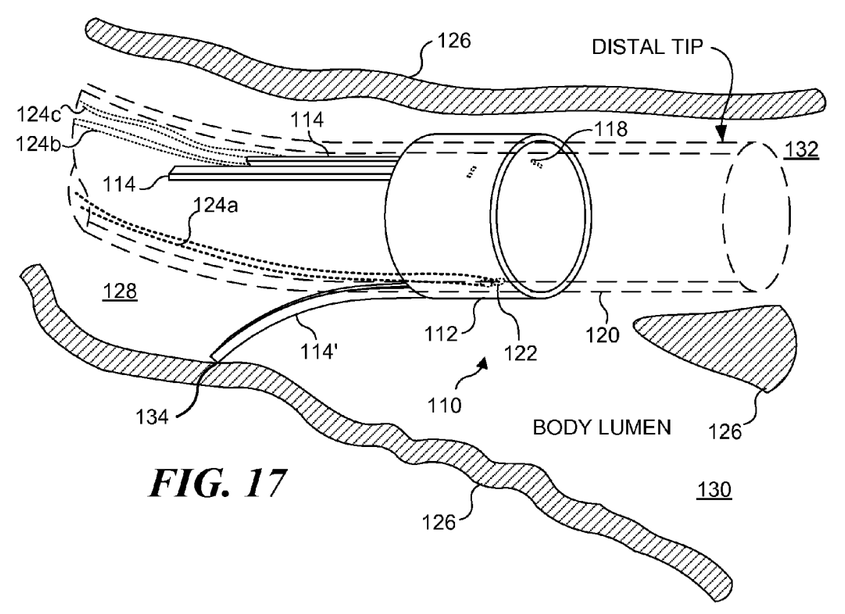
FIG. 17 is a schematic isometric view of the exemplary collar of FIG. 16 being used on a catheter (shown in phantom view) to deflect the distal tip of the catheter into a selected body lumen at a branch point.

FIGS. 16 and 17 illustrate an exemplary embodiment 110 intended to be used with a conventional catheter (fitted with electrical contacts and leads to selectively energize actuators 114). Embodiment 110 includes a collar 112 having an internal diameter sufficiently large to snugly slide over the outer surface of a catheter with which this embodiment is to be used, and then to be affixed at the desired position, using an appropriate adhesive or other suitable fastening technique. It is also contemplated that collar 112 may be removably attached to the catheter.

Collar 112 includes three actuators 114 in this exemplary embodiment, and the actuators are circumferentially spaced-apart around the interior of the collar. Actuators 114 are generally elongate strips of a bimorph material such as SMA, SMP, or EAP, which has two shape configurations. For example, the SMA can be Nitinol, which changes shape as the alloy is heated sufficiently by an electrical current to change from its Martensitic phase to its Austenitic phase. As shown in FIG. 16, an actuator 114' has been actuated with an electric current and has changed from a first shape configuration that is radially compact (like that of actuators 114) to its second shape configuration in which the free end of the actuator extends radially outwardly from the exterior surface of a catheter on which collar 112 has been fastened.

Since the outwardly extending free ends of each actuator may damage adjacent tissue within a patient's body, a soft pliable material 116, formed of a soft plastic, for example, may optionally be fitted over the free ends of actuators 114, so that the soft pliable material 116 contacts the tissue, instead of the end of the actuator.

FIG. 17 schematically illustrates how embodiment 110 is used in connection with a catheter 120, which is shown in phantom view in this Figure. Internal electrical contacts 118 formed on the inwardly facing surface of each actuator 114, are disposed within collar 112 so as to contact corresponding electrical contacts 122, which are formed on the exterior surface of catheter 120. Contacts 122 are connected to electrical leads 124a, 124b, and 124c. These electrical leads extend proximally through catheter 120 within separate lumens (not shown in this Figure) and are connected to an external electrical current source (such as electrical current source 83, which is shown in FIG. 10). One or more of actuators 114 can be selectively actuated by closing switches (not shown) to apply electrical current to specific one or more of the actuators, causing the actuator that is thus heated by electrical current to change to its second shape configuration (i.e., actuator 114') and thereby apply a force against adjacent tissue to deflect the distal tip of catheter 120 in a desired direction, as shown in FIG. 17. In the simple example illustrated in this Figure, catheter 120, which is fitted with embodiment 110, has been advanced through a body lumen 128 defined by tissue 126. By selectively actuating the actuator, actuator 114' assumes its second shape configuration, so that its outwardly extending end 134 applies a force against adjacent tissue 126, thereby deflecting the distal tip of catheter 120 into a lumen 132, so that the catheter can be advanced into that lumen, instead of into a body lumen 130. The deflection of the distal tip can also be employed to direct a scanning mechanism within the distal tip toward a desired site within the body of a patient, enabling that site to be imaged or be diagnosed, or to receive therapy.

Figures 18, 19, 21:
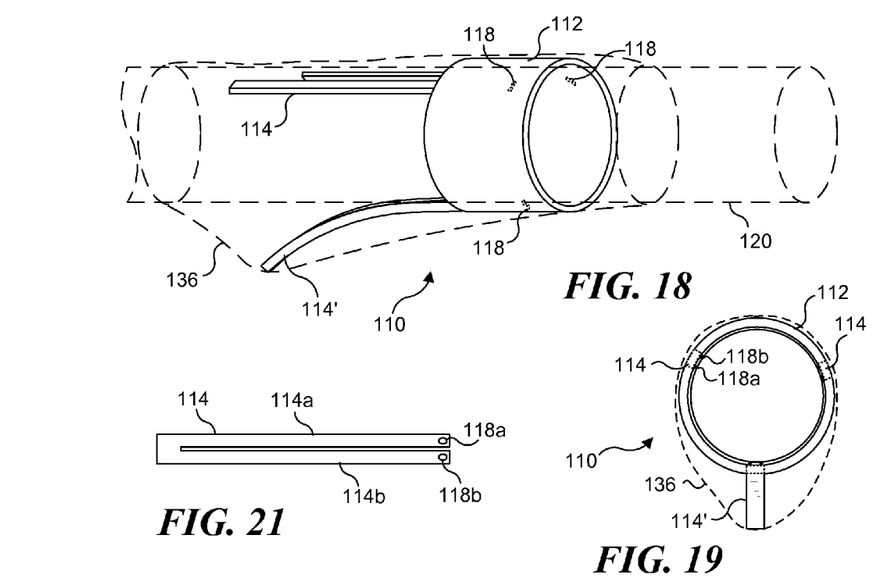
FIG. 18 is an isometric side elevational view of the exemplary collar of FIGS. 16 and 17, but showing an embodiment that includes a balloon or sheath that encompasses the actuators.
FIG. 19 is a cross-sectional view of the exemplary embodiment of FIG. 18.
FIG. 21 is a plan view of an exemplary embodiment of one of the actuators used in the embodiments that include a collar, such as is shown in FIG. 16.

FIGS. 18 and 19 illustrate a first alternative for protecting tissue from hanging up on or being damaged by the free ends of actuators 114, particularly when the actuated to extend really outwardly as actuator 114'. As shown in this schematic view, catheter 120 is fitted with a sheath 136 that fully encompasses embodiment 110, including the free ends of actuators 114. Actuator 114', which has been actuated and extends radially outwardly applies its force to the interior surface of sheath 136, which transfers the force to any adjacent tissue within a patient's body. When not actuated, actuators 114 are covered by sheath 136, so that as the catheter fitted with embodiment 110 is inserted or withdrawn through a lumen within a patient's body, the free ends of the actuators do not unintentionally engage (or hang up on) tissue or anatomical structures within the patient's body.

Figures 20, 22:
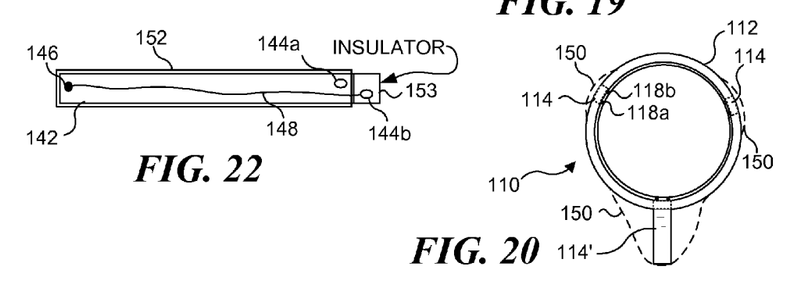
FIG. 20 is a cross-sectional view of an alternative exemplary embodiment wherein each of the plurality of actuators is enclosed within a separate protective sheath or balloon.
FIG. 22 is a plan view of an exemplary embodiment of an alternative exemplary embodiment of an actuator.

Instead of encompassing all of actuators 114 within single sheath 136, a plurality of separate sheaths 150 can be provided, each sheath separately encompassing only one of the actuators, as illustrated in FIG. 20. Sheaths 136 and 150 can be formed of an elastomeric material, such as a suitable plastic or a synthetic rubber that is biocompatible.

FIGS. 21 and 22 illustrate alternative configurations for the actuators used on embodiment 110. In FIG. 21, it will be noted that actuator 114 is shaped much like a hairpin, with two elongate legs 114a and 114b extending generally in parallel. Leg 114a includes an electrical contact 118a, while leg 114b includes an electrical contact 118b. Electrical contacts 118a and 118b enable separate connection to corresponding electrical contacts on the exterior surface of a catheter over which collar 112 is fitted. Electrical current thus flows into one of these two legs and out of the other through the contacts, to heat the actuator when it is selectively actuated.

FIG. 22 illustrates an actuator 142 that is formed of a single elongate strip of the bimorph material, but on the end attached to collar 112, actuator 142 includes an insulator tab 153 and is enclosed in a plastic sheath 152. An electrical contact 146 is formed on the free end of the actuator and is connected to an electrical lead 148, which extends along the length of the actuator to connect with electrical contact 144b. Electrical contact 144b is disposed on insulator tab 153. An electrical contact 144a is formed on the opposite end of actuator 142 (opposite to the end at which electrical contact 146 is disposed). When collar 112 is fitted to an appropriate catheter having corresponding electrical contacts disposed on its exterior surface, electrical contacts 144a and 144b mate with the electrical contacts on the catheter. When actuator 142 is actuated, an electrical current flows through electrical contact 144a, through the bimorph material, out electrical contact 146, through electrical lead 148, and out through electrical contact 144b. Insulator tab 153 prevents an electrical short circuit between electrical contacts 144a and 144b.

Figure 23:
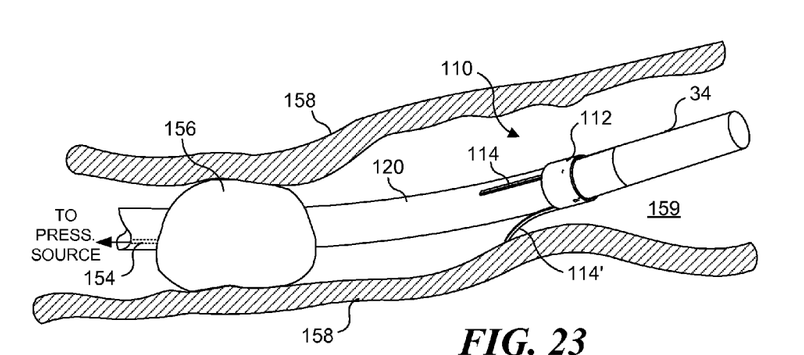
FIG. 23 is a schematic view of a catheter employing the collar shown in FIG. 16, illustrating how a balloon can be included on a catheter proximally of the actuators and inflated to anchor the catheter in a body lumen when deflecting the distal tip of the catheter.

FIG. 23 illustrates how a balloon 156 disposed proximal of embodiment 110 on catheter 120 can be inflated when supplied with a pressurized fluid through a lumen 154. Balloon 156 is inflated with the pressurized fluid within a body lumen 159 sufficiently to contact tissue 158. The inflated balloon thus stabilizes the catheter by anchoring it relative to the tissue, when one or more of actuators 114 are actuated (as is actuator 114' in this Figure) to deflect distal tip 34 of the catheter in a desired direction within body lumen 159.

Figure 24:
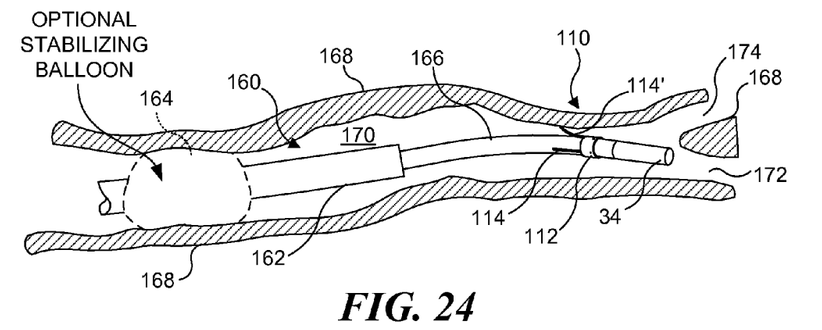
FIG. 24 is a schematic view of an exemplary catheter having a mother scope and a daughter scope, showing how the an optional balloon on the mother scope can be inflated to anchor it within a body lumen while the distal end of the daughter scope is deflected by one or more actuators on a collar attached to the daughter scope.
Figure 25:
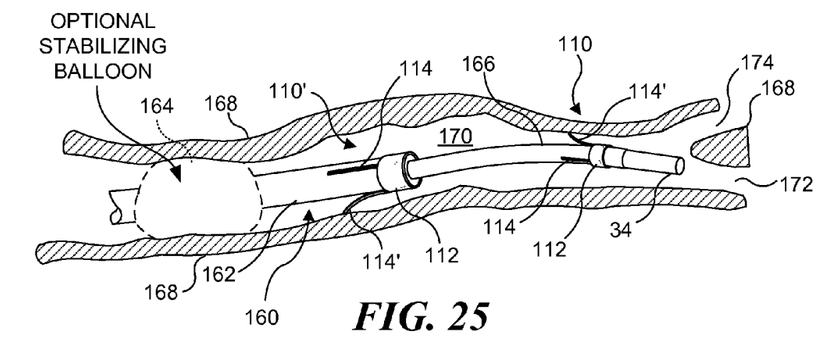
FIG. 25 is a schematic view of the catheter like that shown in FIG. 24, but wherein the mother scope and the daughter scope each includes a collar for providing deflection of the distal end of the mother scope and of the distal end of the daughter scope

FIGS. 24 and 25 illustrate two related embodiments of a catheter 160 that includes a mother scope 162, and a daughter scope 166 that extends distally of the mother scope. The mother scope can optionally be stabilized within a body lumen 170 defined by tissue 168, by inflating an optional balloon 164. The daughter scope is advanced and guided into a desired body lumen 172 (rather than into a body lumen 174, by selectively actuating actuator 114', as shown in FIG. 24, so that distal tip 34 is deflected as a result of the force applied by actuator 114' against tissue 168.

The alternative exemplary embodiment of catheter 160 shown in FIG. 25 is much the same as the embodiment shown in FIG. 24, but in this alternative, mother scope 162 is also fitted with an embodiment 110' that includes collar 112 and one or more of the actuators 114 attached to the collar. In the example of this Figure, one actuator 114' has been actuated to deflect the distal end of the mother scope by applying a force against adjacent tissue 168. It will also be understood that the embodiment fitted to the distal end of daughter scope 166 can optionally be omitted, and embodiment 110' on mother scope 162 can then be used to provide deflection of the mother scope without directly deflecting the distal end of the daughter scope.

Figure 26:
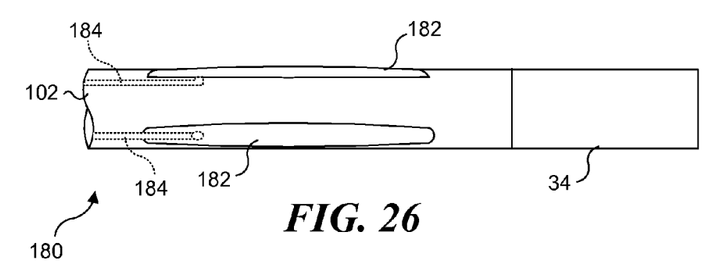
FIG. 26 is a schematic view of an exemplary embodiment of a catheter that includes a plurality of longitudinally extending balloons disposed at spaced-apart positions around the circumference of the catheter.
Figure 27:
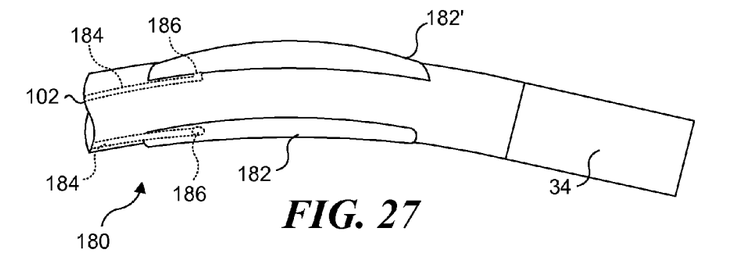
FIG. 27 illustrates the exemplary embodiment of FIG. 26, showing how the distal end of the catheter is deflected by selectively inflating one or more of the longitudinally extending balloons.

An exemplary embodiment of a catheter 180 is illustrated in FIGS. 26 and 27. Catheter 180 is flexible, just as the other embodiments discussed above, and includes a plurality of elongate balloons 182 (but may include only a single elongate balloon, if less directional control is required) that are disposed at circumferentially spaced-apart positions on the outer surface of catheter 180 and which extend along its longitudinal axis. Alternatively, although not specifically shown, it is contemplated that the elongate balloons 182 can instead be embedded in the outer skin or sheath of the catheter. Lumens 184 extend to the proximal end of the catheter and each is coupled through a valve to an external source of pressurized fluid (the valve and external pressure source are not shown but are similar to valve 54 and pressure source 56, shown in FIG. 5), such as air or saline solution, which can be selectively coupled in fluid communication to any selected one of balloons 182 by opening the appropriate valve. Before the pressurized fluid is applied to any balloon 182, catheter 182 will be generally straight, as shown in FIG. 26. However, FIG. 27 illustrates how the distal end of catheter 180 is deflected when pressurized fluid is selectively applied to balloon 182', causing it to expand longitudinally and apply a force that acts like a piston to bend the distal end of catheter 180, as shown. The same result can be obtained if balloon 182' is embedded in the outer skin or sheath of catheter 180.

Figure 28:
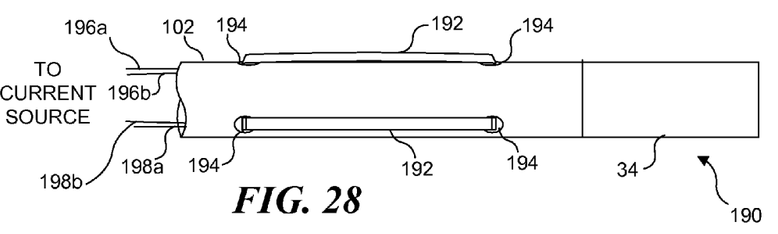
FIG. 28 is a schematic view of an exemplary embodiment of a catheter that includes a plurality of longitudinally extending wires or strips that are attached to the outer surface of the catheter at opposite ends and can be selectively actuated by being heated with an electrical current to change shape.
Figure 29:
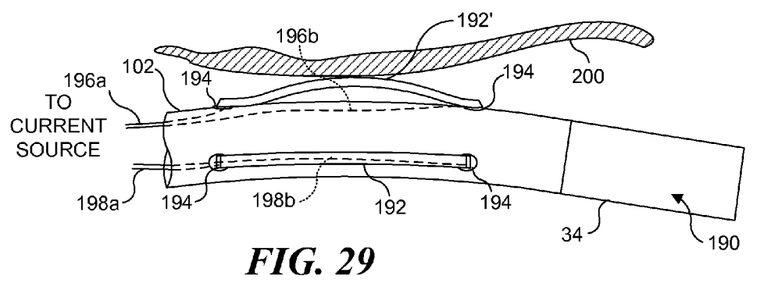
FIG. 29 illustrates the exemplary embodiment of FIG. 28 after one or more of the longitudinally extending wires or strips have been actuated and has elongated to bow outwardly away the outer surface of the catheter into contact with adjacent tissue, deflecting the distal end of the catheter.

FIGS. 28 and 29 illustrate an exemplary embodiment of a catheter 190 that can include a single elongate wire or strip 192, but which is illustrated in this embodiment, as including a plurality of elongate wires or strips 192 that are disposed at circumferentially spaced-apart positions on the outer surface of catheter 190. Opposite ends of each elongate wire or strip 192 are attached with adhesive or otherwise bonded to the outer surface of the catheter at pads 194. Electrical leads 196a and 196b, which extend through catheter 190, are respectively electrically connected to opposite ends of one of the elongate wire or strip, while electrical leads 198a and 198b, which also extend through the catheter, are respectively coupled to another of the elongate wire or strip. The other ends of the electrical leads are connected through switches to a conventional power source (not shown in this Figure, but similar to power source 83 in FIG. 10), so that electrical current can be selectively applied to heat one or more of the elongate wires or strips 192 sufficiently to actuate the one or more elongate wires or strips, causing it to change shape. The elongate wires or strips are each made of a material, such as an SMA alloy or an EAP, that changes shape and/or length, when heated, or an EAP, which changes shape of size when electrically stimulated, e.g., by application of an appropriate electrical potential. As shown in FIG. 28, when no electrical current (or other stimulation) is applied, catheter 190 is straight. When an electrical current (or other stimulation) is applied to any elongate wire or strip 192', it expands in length and bows outwardly away from the outer surface of the catheter. This expansion in length of elongate wire or strip 192' tends to deflect the distal tip of the catheter away from the side of catheter 190 on which the heated elongate wire or strip is disposed and also, can apply a force against an adjacent tissue surface 200 to further deflect the catheter distal end, as shown in FIG. 29.

Additional alternative exemplary embodiments for deflecting the distal end of a catheter comprise electromechanical actuators, such as piezoelectric composites that are used in larger-scale actuator applications, or bimorph thermal actuators, which are more suitable for use in smaller-scale micro-electromechanical system (MEMS) actuators. One example of a piezo-composite is available from Face International Corporation, Norfolk, Va. and comprises a thin layer uni-morph ferroelectric driver that can produce extraordinarily large deflections in a cantilever actuator, like actuators 114/114' shown in FIGS. 16-25. Smaller versions of this commercially-available electromechanical actuator can thus be used as tip displacement actuator 114 in such exemplary embodiments.

Figure 30A:
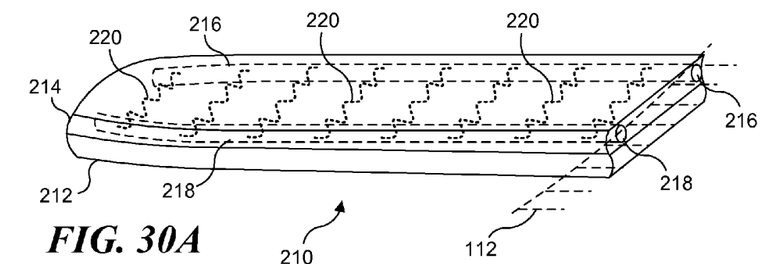
FIGS. 30A and 30B illustrate the outwardly extending portions of an exemplary bimorph thermal actuator before actuation (FIG. 30A) and after being actuated with an electric current (FIG. 30B), to apply a force against adjacent tissue to deflect the distal end of the catheter.
Figure 30B:
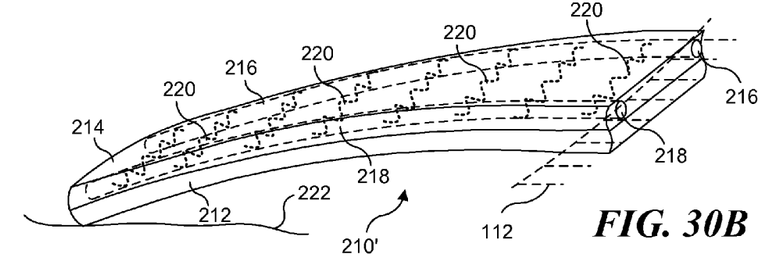

In contrast, a larger version of a MEMS bimorph thermal actuator 210 can be used as a tip displacement actuator, as shown in FIGS. 30A and 30B. FIG. 30A illustrates MEMS bimorph thermal actuator 210 before it is actuated. This actuator comprises a layer of material 212 that is bonded to a layer of a material 214. Materials 212 and 214 are dissimilar and have substantially different coefficients of thermal expansion and elastic moduli. A differential expansion of dissimilar materials 212 and 214 due to heating with an electrical current results in a curling motion of the actuator. The differential rate of change of linear strain of dissimilar materials 212 and 214 with temperature thus causes the deflection illustrated for MEMS bimorph thermal actuator 210' in FIG. 30B. The outwardly extending end of the MEMS bimorph thermal actuator can apply a force against adjacent tissue 222 to deflect the distal end of the catheter in a desired direction.

To heat the dissimilar materials during the actuation, MEMS bimorph thermal actuator 210 includes a plurality of heating resistors 220 (comprising a material having a desired ohmic heating characteristic), which can be disposed as third layer in the actuator or, as shown, can be embedded in one of the layers of materials 212 and 214. Heating resistors 220 are coupled to a pair of wires or conductors 216 and 218, which also comprise a load-bearing backbone for the actuator. Optionally, the layers of materials 212 and 214, and conductors 216 and 218 can be extended in length to form a longer lever arm than that shown in FIGS. 30A and 30B. All layers shown in FIGS. 30A and 30 have the same surface area, but optimized curling response can be achieved by using the cross-sectional and surface areas, cantilever geometry, and resistor values as design variables. MEMS bimorph thermal actuator 210 can be directly connected to the outer surface of the catheter or can extend from collar 112 (like actuators 114 in FIG. 18) as shown in the exemplary embodiment of FIGS. 30A and 30B.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A catheter having a distal tip that can be selectively deflected in a desired direction, comprising:
   (a) an elongate flexible shaft having a distal end where the distal tip of the catheter is disposed, a proximal end, and an outer surface;
   (b) an actuator, at least a portion of which is disposed proximate to the outer surface, and which is selectively actuatable either by changing a temperature of the actuator or by applying an electric potential, to provide a directed force that causes the distal end of the catheter to deflect in the desired direction further comprising a sheath, the sheath comprising a non-extendible balloon that is disposed around the outer surface of the elongate flexible shaft, encompassing the actuator; and
   (c) a source of electrical energy for selectively actuating the actuator by changing the temperature of the actuator or by providing the electric potential, to deflect the distal end in the desired direction.

2. The catheter of claim 1, wherein the actuator comprises a bimorph actuator that has two shape configurations, including a first configuration in which the bimorph actuator is radially compact, and a second configuration in which the bimorph actuator extends radially outwardly from the outer surface of the elongate flexible shaft, wherein the bimorph changes between the first configuration and the second configuration in response to a change in temperature of the bimorph actuator.

3. The catheter of claim 1, wherein the bimorph actuator comprises a material selected from the group consisting of:
   (a) a shape memory alloy;
   (b) a piezo-composite;
   (c) a plurality of dissimilar materials having substantially different coefficients of thermal expansion, bonded together;
   (d) a shape memory polymer; and
   (e) an electro-active polymer.

4. The catheter of claim 2, wherein in the second configuration, the bimorph actuator applies the directed force against an interior surface of the sheath, which is configured to transfer the force to any adjacent anatomical structure within a body of a patient, so as to deflect the distal end of the elongate flexible shaft away from the adjacent anatomical structure in the desired direction, the sheath providing a smooth surface to facilitate advancement and withdrawal of the catheter through a body lumen.

5. The catheter of claim 1, wherein the actuator comprises an elongate strip of a material that changes shape when selectively actuated, the elongate strip of material being attached to the outer surface of the elongate flexible shaft at opposite ends and when actuated, changing shape so that a portion of the elongate strip of material disposed between the opposite ends moves outwardly away from the outer surface of the elongate flexible shaft, causing the distal end of the elongate flexible shaft to deflect in the desired direction.

6. The catheter of claim 1, further comprising:
   (a) a balloon that is configured to expand around the outer surface of the elongate flexible shaft and which is disposed proximal of the actuator; and
   (b) a lumen extending through at least a portion of the elongate flexible shaft for conveying a pressurized fluid from a source to inflate the balloon so that a diameter of the balloon increases sufficiently to contact an adjacent anatomical structure within a body of a patient, the balloon that is thus inflated exerting a force on the adjacent anatomical structure that stabilizes the catheter relative to the adjacent anatomical structure while the distal end of the elongate flexible shaft is being deflected in the desired direction.

7. The catheter of claim 1, further comprising a mother scope that extends generally from the proximal end of the catheter and includes a distal end that is disposed at an intermediate position along a length of the catheter, and a daughter scope that extends distally from the distal end of the mother scope, wherein the daughter scope includes the distal end of the elongate flexible shaft, and the actuator to selectively deflect the distal end of the daughter scope.

8. The catheter of claim 1, further comprising a mother scope that extends generally from the proximal end of the catheter and includes a distal end that is disposed at an intermediate position along a length of the catheter, and a daughter scope that extends distally from the distal end of the mother scope, wherein the mother scope includes another actuator that is selectively coupled to the source of electrical energy, to selectively deflect the distal end of the mother scope either as a function of a change in temperature of the other actuator selectively caused by selectively applying electrical energy to produce heat that changes the temperature of the other actuator, or by applying the electric potential to activate the other actuator.

9. The catheter of claim 1, wherein the elongate shaft is rotatable about its longitudinal axis, to position the actuator in a desired orientation so when selectively actuated, the actuator deflects the distal tip of the catheter in the desired direction.

10. The catheter of claim 1, wherein the distal tip includes an imaging device that emits light for producing an image used for visualizing a pathway along which the catheter is being advanced.

11. A catheter having a distal tip that can be selectively deflected in a desired direction, comprising:
    (a) an elongate flexible shaft having a distal end where the distal tip of the catheter is disposed, a proximal end, and an outer surface;
    (b) a plurality of actuators, at least a portion of each actuator being disposed externally of the outer surface, at circumferentially spaced-apart positions, and being selectively actuatable either by changing a temperature of the actuator or by applying an electric potential to the actuator, to provide a directed force that causes the distal end of the catheter to deflect in the desired direction, wherein a sheath comprising a non-extendible balloon is disposed around the outer surface of the elongate flexible shaft, encompassing the plurality of actuators; and
    (c) a source of electrical energy for selectively actuating one or more of the plurality of actuators either by changing the temperature of said one or more of the plurality of actuators, or by applying the electric potential, to deflect the distal end in the desired direction.

12. The catheter of claim 11, wherein each of the plurality of actuators comprises a bimorph actuator that has two shape configurations, including a first configuration in which the bimorph actuator is radially compact, and a second configuration in which the bimorph actuator extends radially outwardly from the outer surface of the elongate flexible shaft, wherein the bimorph changes between the first configuration and the second configuration in response to a change in temperature of the bimorph actuator, or in response to application of the electric potential to the bimorph actuator.

13. The catheter of claim 12, wherein each bimorph actuator comprises a material selected from the group consisting of:
    (a) a shape memory alloy;
    (b) a piezo-composite;
    (c) a plurality of dissimilar materials having substantially different coefficients of thermal expansion, bonded together;
    (d) a shape memory polymer; and
    (e) an electro-active polymer.

14. The catheter of claim 12, wherein each bimorph actuator that is selectively activated applies the directed force against an interior surface of the sheath, which is configured to transfer the force to any adjacent anatomical structure within a body of a patient, so as to deflect the distal end of the elongate flexible shaft away from the adjacent anatomical structure in the desired direction, the sheath providing a smooth surface to facilitate advancement and withdrawal of the catheter through a body lumen.

15. The catheter of claim 11, wherein each actuator comprises an elongate strip of a material that changes shape when selectively actuated, the elongate strip of material being attached to the outer surface of the elongate flexible shaft at opposite ends and when actuated, changing shape so that a portion of the elongate strip of material disposed between the opposite ends moves outwardly away from the outer surface of the elongate flexible shaft, causing the distal end of the elongate flexible shaft to deflect in the desired direction.

16. The catheter of claim 11, further comprising:
    (a) a balloon that is configured to expand around the outer surface of the elongate flexible shaft and is disposed proximal of the plurality of actuators; and
    (b) a lumen extending through at least a portion of the elongate flexible shaft for conveying a pressurized fluid from a source to inflate the balloon so that a diameter of the balloon increases sufficiently to contact an adjacent anatomical structure within a body of a patient, the balloon that is thus inflated exerting a force on the adjacent anatomical structure that stabilizes the catheter relative to the adjacent anatomical structure while the distal end of the elongate flexible shaft is being deflected in the desired direction.

17. The catheter of claim 11, further comprising a mother scope that extends generally from the proximal end of the catheter and includes a distal end that is disposed at an intermediate position along the catheter, and a daughter scope that extends distally from the distal end of the mother scope, wherein the daughter scope includes the distal end of the elongate flexible shaft, and the plurality of actuators to selectively deflect the distal end of the daughter scope.

18. The catheter of claim 10, further comprising a mother scope that extends generally from the proximal end of the catheter and includes a distal end that is disposed at an intermediate position along a length of the catheter, and a daughter scope that extends distally from the distal end of the mother scope, wherein the mother scope includes another plurality of actuators, each of which is selectively coupled to the source of electrical energy, to selectively deflect the distal end of the mother scope in a desired direction as a function of a change in temperature of the other actuator selectively caused by selectively applying electrical energy to produce heat that changes the temperature of the other actuator, or in response to application of an electric potential to the other actuator that causes it to change shape.

19. The catheter of claim 11, wherein the distal tip includes an imaging device that emits light for producing an image used to visualize a pathway along which the catheter is being advanced.

20. Apparatus for controllably selectively deflecting a distal tip of a catheter in a desired direction, comprising:
    (a) a collar configured to be disposed around the outer surface of a catheter, adjacent to a distal tip of the catheter; and
    (b) a plurality of actuators disposed on the collar, wherein a sheath comprising a non-extendible balloon is disposed around the plurality of actuators, each actuator of the plurality of actuators being selectively actuatable by changing a temperature of the actuator, causing the actuator to change shape and to produce a directed force outwardly of the collar to deflect a distal tip of a catheter in a desired direction.

21. The apparatus of claim 20, further comprising means for selectively actuating each actuator disposed on the collar, by changing the temperature of the actuator, to produce the directed force.

22. The apparatus of claim 20, wherein each of the plurality of actuators comprises a bimorph actuator that is selectively actuated to change between two shape configurations, a first configuration of the bimorph actuator being substantially more radially compact relative to the collar than a second configuration, the bimorph actuator being thus adapted to produce the directed force when actuated in response to a change in temperature of the bimorph actuator, to change between the first configuration and the second configuration.

23. The apparatus of claim 22, wherein each bimorph actuator comprises a material selected from the group consisting of:
    (a) a shape memory alloy;
    (b) a piezo-composite;
    (c) a plurality of dissimilar materials having substantially different coefficients of thermal expansion, bonded together;
    (d) a shape memory polymer; and
    (e) an electro-active polymer.

24. The apparatus of claim 22, wherein in the second configuration, each bimorph actuator that is selectively activated applies the directed force against an interior surface of the sheath, which is configured to apply the directed force to any adjacent anatomical structure within a body of a patient, so as to deflect a distal tip of a catheter away from the adjacent anatomical structure in the desired direction, the sheath providing a smooth surface to facilitate advancement and withdrawal of a catheter through a body lumen.

25. The apparatus of claim 20, further comprising electrical contacts disposed on the collar and configured to couple to corresponding electrical contacts on a catheter for coupling an electrical current to each of the plurality of actuators, the electrical current being selectively applied to an actuator to actuate it by changing its temperature with heat produced by the electrical current.

26. The apparatus of claim 20, further comprising a plurality of pliable members that are each relatively substantially softer than the plurality of actuators, a pliable member being disposed over an end of each actuator to minimize damage to tissue against which the directed force is applied to deflect a distal tip of a catheter.

27. A method for selectively deflecting a distal tip of a catheter in a desired direction, comprising the steps of:
    (a) providing a plurality of actuators disposed at circumferentially-spaced apart positions around an outer surface of the catheter, wherein at least a portion of each of the plurality of actuators is disposed externally of an outer surface of the catheter;
    (b) providing protective sheath comprising a non-extendible balloon that is disposed around and encompasses the plurality of actuators; and
    (c) selectively actuating at least one of the plurality of actuators either by changing a temperature of the actuator causing the actuator to change shape, or by applying an electric potential to the actuator that causes the actuator to change shape, and thereby, to produce a directed force that deflects the distal tip of the catheter in the desired direction, the directed force being developed externally of an outer surface of the catheter.

28. The method of claim 27, wherein the step of selectively actuating comprises the step of applying an electrical current that produces heat to change a temperature of a bimorph actuator comprising each of the plurality of actuators that is to be actuated, or applying the electric potential to each of the plurality of actuators that is to be actuated.

29. The method of claim 28, wherein each bimorph actuator, when actuated, changes between a first configuration and a second configuration in response to the change in temperature of the bimorph actuator, or in response to application of the electric potential, the second configuration applying the directed force so as to deflect the distal tip of the catheter.

30. The method of claim 29, wherein the bimorph actuators bend radially outwardly when actuated to change from the first configuration to the second configuration.

31. The method of claim 30, wherein when in the second configuration, the bimorph actuators are adapted to apply the directed force against an anatomical structure within a body of a patient, biasing the distal tip of the catheter to generally deflect in an opposite direction from that in which the directed force is applied.

32. The method of claim 27, further comprising the step of employing the protective sheath to facilitate insertion and withdrawal of the catheter through a body lumen.

33. The method of claim 27, wherein each of the plurality of actuators comprises an elongate strip that extends longitudinally along the catheter, proximate to the outer surface of the catheter, the elongate strip comprising a material that changes state when heated, and wherein the step of selectively actuating comprises the step of selectively applying an electrical current to the at least one actuator to cause the elongate strip to compress axially as the material from which it is made changes from one state to another in response to heating caused by the electrical current.

34. The method of claim 27, further comprising the step of using an imaging device disposed proximate to the distal tip of the catheter, for producing an image of a pathway along which the catheter is being advanced, to assist in determining which of the plurality of actuators to selectively actuate.

* * * * *